United States Patent [19]

Konoki et al.

[11] 4,218,397

[45] Aug. 19, 1980

[54] METHOD FOR ELIMINATING THE EXPLOSIBILITY OF TAIL GAS FROM THE UREA SYNTHESIS PLANT

[75] Inventors: Keizo Konoki, Tokyo; Michio Nobue, Funabashi, both of Japan

[73] Assignees: Mitsui Toatsu Chemicals, Inc.; Toyo Engineering Corporation, both of Tokyo, Japan

[21] Appl. No.: 39,889

[22] Filed: May 17, 1979

[30] Foreign Application Priority Data

May 20, 1978 [JP] Japan .................................. 53/60365

[51] Int. Cl.² .......................................... C07C 126/02
[52] U.S. Cl. ................................. 260/555 A; 423/359
[58] Field of Search ..................... 260/555 A; 423/359

[56] References Cited

U.S. PATENT DOCUMENTS

| | | | |
|---|---|---|---|
| 3,120,563 | 2/1964 | Bongard | 260/555 A |
| 3,488,293 | 1/1970 | Hong | 260/555 A |
| 3,539,292 | 11/1970 | Huebler | 423/359 |
| 3,691,729 | 9/1972 | De Rooy | 260/555 A |

FOREIGN PATENT DOCUMENTS 7510544 10/1977 Netherlands ........................ 260/555 A

OTHER PUBLICATIONS

*Chemical Abstracts*, vol. 86, 1977, No. 16275e.

*Primary Examiner*—Brian E. Hearn
*Attorney, Agent, or Firm*—Blanchard, Flynn, Thiel, Boutell & Tanis

[57] ABSTRACT

The tail gas from the urea synthesis plant is rendered non-explosive by adding thereto a purge gas that is obtained from the ammonia synthesis plant that is usually installed closed to the urea synthesis plant and used for synthesis of ammonia used as starting material for the urea synthesis.

1 Claim, 1 Drawing Figure

METHOD FOR ELIMINATING THE EXPLOSIBILITY OF TAIL GAS FROM THE UREA SYNTHESIS PLANT

This invention relates to a process for preparing urea. More particularly, it relates to the elimination of explosibility of a gaseous mixture containing gaseous components that should be removed from an urea synthesis plant.

Urea is synthesized under elevated temperatures and pressures from ammonia and carbon dioxide as starting materials, through a reaction shown by the following two formulae:

$$2NH_3 + CO_2 \rightleftharpoons NH_2CO_2NH_4 \quad (1)$$

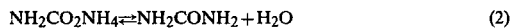

$$NH_2CO_2NH_4 \rightleftharpoons NH_2CONH_2 + H_2O \quad (2)$$

The urea synthesis is usually carried out at a pressure of 140 to 300 atm. and a temperature of 180° to 220° C. in the presence of excess ammonia. The rate of conversion from carbon dioxide to urea in the reactor ranges from 50 to 80%.

Accordingly, the effluent from the reactor comprises urea, ammonia carbamate, ammonia, water and a small amount of other components.

The effluent from the reactor is processed by a plurality of separating steps, in which urea is separated from excess ammonia, a gaseous mixture of ammonia, carbon dioxide and steam have been produced upon decomposition of ammonium carbamate and a small amount of the other components. The gaseous mixture separated during this separating step is absorbed in a solvent and fed back to the reactor. The ammonia and carbon dioxide to be used as starting materials for the urea synthesis usually contain, for example, nitrogen, hydrogen, carbon monoxide, methane and other impurities, in the gaseous or liquid state. The components in the effluent that have not been converted into urea are transferred back to the reactor, as described above, for circulation through the reaction system. Thus, the above impurities are not only useless for the urea synthesis, but rather tend to lower the operating efficiency, because they are gradually accumulated in the system unless discharged from the system.

Thus, these impurities are discharged from the system, together with as small an amount of useful components as possible.

When an equipment for the urea synthesis is made from a corrosion-resistant material, or provided with lining of such a material, a small amount of oxygen or air is introduced into the system as a passivator to prevent hot strongly corrosive ammonium carbamate from corroding the synthesis equipment heavily. A minor portion of the air or oxygen thus introduced into the system is dissolved effectively in the process liquid stream, but the major portion thereof is discharged from the system along with the above mentioned impurities.

During absorption of ammonia and carbon dioxide by the solvent, the impurities contained in the gas phase in the synthesis equipment vary in concentration. Thus, the hydrogen and ammonia in the impurities and the oxygen that is added in a sufficient amount for the purpose of passivation exist simultaneously in the gaseous mixture during or after the absorption. Hence, the gaseous mixture tends to be explosive. If explosion occurs in the apparatus, the high pressure prevalance in the apparatus is further increased to a value which may amount to 10 times the original pressure instantaneously. If the apparatus should have sufficient strength to withstand such a shock of explosion, the design pressure should be selected to a range of 100 to 3000 atom. for the design absorption pressure of ammonia and carbon dioxide in the range from 10 to 220 atom. Such high pressure apparatuses tend to be rather expensive.

For elimination of explosibility, the hydrogen in the impurities may be oxidized by a catalytic reaction. However, the oxydation catalysts used for such purpose are rather expensive because noble metals are used as catalytically active components. Moreover, for oxidation of hydrogen to less than its explosive percentage, a large amount of air or oxygen must be introduced into the feed stock, carbon dioxide. The air supplied to such purposes result in increased amounts of gases and impurities in the system which in turn tend to lower the conversion rate in the reactor and increase the costs of equipment used in the absorption system. On the other hand, if oxygen is supplied to such purpose, a device for continuous manufacture of oxygen is necessary to provide in the urea synthesis system, which means an additional construction cost.

As means for preventing explosion, a prior art (Jap. pat. Publication No. 43800/1977) contemplates to provide a pressure buffer zone surrounding the absorption zone and to supply carbon dioxide or a gaseous mixture containing carbon dioxide from the pressure buffer zone for diluting the residual gas mixture in the absorption zone. The gas mixture in the absorption zone is then discharged while its explosibility is restrained partially. This method is, however, not completely satisfactory in removing the risk of generation of an explosive gas mixture in the synthesis system.

It is also known to use nitrogen as diluting agent. This method is effective when the partial oxidation method is used for gasification of feedback in the ammonia production process and a larger device for producing nitrogen is available. However, with the steam reforming process, for gasification of feedstock, the nitrogen production device is necessarily small and has to be supplemented at an additional cost for preparation of nitrogen for dilution.

Thus, the conventional method for preventing explosion of tail gas provided from the urea synthesis process may be conducted by sufficiently elevating the pressure resistancy of the apparatus; catalytically oxidizing combustible gas components; or providing a pressure buffer zone by adding carbon dioxide or similar noncombustible gases as diluent. These methods are not desirable from consideration of equipment costs. With the use of carbon dioxide as diluent, it is necessary to provide means to recover carbon dioxide and to supply steam and cooling water to the system. Moreover, sufficient prevent of explosion can not be expected from any of these known methods.

SUMMARY OF THE INVENTION

This invention contemplates to provide for a method for eliminating the explosibility of tail gas. The method is free from the aforementioned inconveniences. In the conventional practice, either a noncombustible gas is used as a diluent for explosive gases, or the combustible gas components contained in the process stream are converted into noncombustible gases. According to the present invention, non of these conventional methods is used, but combustible gases are used for eliminating the explosibility of tail gases.

The ammonia used as starting material for urea synthesis is produced in a synthesis plant neighboring to the urea synthesis plant. The hydrogen and nitrogen that are not converted into ammonia are transferred back to the ammonia synthesis reactor. Methane and other useless gas components, these impurities accompanying hydrogen and nitrogen used as starting material, tend to be accumulated in this circulating stream. Therefore, a purge gas containing considerable amounts of hydrogen and nitrogen is discharged from the circulating stream for removal of these useless gas components. Such purge gas is usually consumed as fuel.

It has now been discovered that addition to this purge gas from the ammonia sythesis circulating stream to the tail gas of the urea synthesis process enables complete elimination of the explosibility of the tail gas.

Thus, the present invention resides in a method for eliminating the explosibility in tail gas from the urea synthesis process comprising the steps of decomposing ammonium carbamate contained in the effluent from the urea synthesis reactor to produce a gaseous mixture; absorbing the ammonia and carbon dioxide contained in the gaseous mixture by a solvent and transferring the thus absorbed ammonia and carbon dioxide back into the urea synthesis reactor, adding to a residual gas mixture which has not been absorbed by the solvent, i.e. tail gas, a purge gas from an ammonia synthesis circulating system to lower the oxygen concentration in said residual gas mixture and keep the combustible gas concentration beyond the range of explosion.

In order that the residual gas mixture may no longer be explosive, the hydrogen concentration should be lower than 4% or higher than 94% based on oxygen gas. Methane, ammonia and carbon monoxide should be in the ranges of 5 to 61%, 15 to 79% and 15.5 to 94%, respectively. Only these four kind of gases need be considered in practicing the method of the present invention relative to the tail gas of the urea synthesis process.

In other words, the risk of explosion can be removed completely by keeping the oxygen concentration of the tail gas of the urea synthesis process reduced as lower than 4%, the balance being combustible and noncombustible gases.

DESCRIPTION OF A PREFERRED EMBODIMENT

Figure 1:
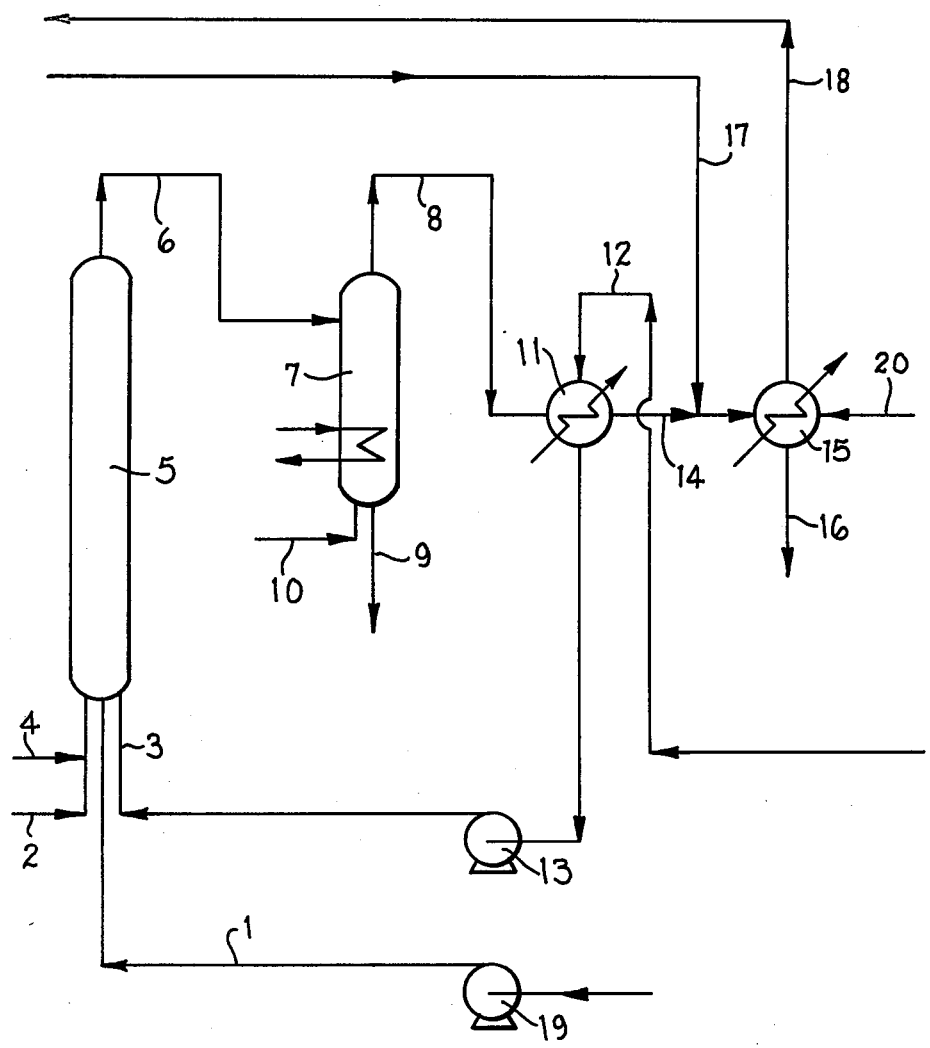
FIG. 1 is a flow sheet showing an embodiment of the present invention.

Ammonia, carbon dioxide and a circulating liquid are supplied to a urea synthesis reactor 5 through pipes 1, 2 and 3, respectively, while a small amount of air is added to the carbon dioxide in the pipe 2 through the pipe 4 to inhibit the corrosion of the synthesis apparatus. The effluent leaving the reactor 5 and consisting of urea, ammonium carbamate, ammonia, water and minor components are supplied via pipe 6 to a decomposer 7. The ammonium carbamate that has not been converted into urea is decomposed in the vessel 7 and an off-gas consisting essentially of carbon dioxide and ammonia is supplied via pipe 8 to an absorber 11. The aqueous urea solution from which ammonium carbamate has been removed is obtained from pipe 9. A small amount of air is introduced via pipe 10 to the vessel 7 for inhibiting corrosion of the synthesis apparatus.

An absorbent solution for carbon dioxide and ammonia such as dilute aqueous solution of ammonia or urea is supplied into absorber 11 via pipe 12 and the carbon dioxide and ammonia thus absorbed are transferred back to the reactor 5 via pipe 3 by means of a pump 13.

A purge gas from the circulating stream of the ammonia synthesis system is supplied to a pipe 14 via pipe 17. The gas mixture thus enriched in hydrogen and free from the risk of explosion is supplied to a scrubber 15 where it is scrubbed with water from pipe 20 for final recovery of ammonia. The residual gas mixture is discharged via pipe 18 and supplied as fuel gas to gasification plant, not shown, for ammonia synthesis gas.

In case that the purge gas from pipe 17 is not supplied to the process, the discharge gas from scrubber 15 consists for instance of 33% of $H_2$, 12% of $O_2$ and 55% of $N_2$, the gas being thus explosive.

With the plant shown, having daily urea throughput of 1,000 tons, the flow from pipe 18 is 420 $Nm^3/hr$. unless the purge gas is supplied from pipe 17. If the purge gas from the ammonia synthesis circulating stream consisting of 61% of $H_2$, 13% of $CH_4$ and 26% of argon and other gases is supplied via pipe 17 at a rate of 980 $Nm^3/hr$., the oxygen concentration of the discharge gas as measured downstream of the point of addition is 3.6% at most, relating to the combustible gas. Thus there is no risk of explosion.

The purge gas should be added to the tail gas stream at its sufficiently upstream position as close to the discharge end as possible, where there is no risk for the tail gas to become an explosive gaseous mixture.

The method of the present invention provides for perfectly reliable prevention of explosion and makes it unnecessary to design the synthesis apparatus with increased pressure resistance sufficient to withstand the explosion. At working of this invention, the components necessary to provide in the conventional synthesis apparatus are a conduit for transport of purge gas from the ammonia synthesis loop and, if desired, a small conduit for returning the tail gas from the urea synthesis apparatus to the ammonia synthesis apparatus.

Therefore, there is no necessity of providing any special devices, furthermore there is no necessity of steam, water, electricity or additional supply.

What is claimed is:

1. A method for eliminating the explosibility of tail gas from the urea synthesis process, which comprises the steps of: decomposing ammonium carbamate contained in the effluent from an urea synthesis reactor to produce a gaseous mixture; absorbing the ammonia and carbon dioxide contained in said gaseous mixture by a solvent and transferring the thus absorbed ammonia and carbon dioxide back into the urea synthesis reactor; and adding to the residual gas mixture which has not been absorbed by the solvent a purge gas available from an ammonia synthesis circulating system to lower the oxygen concentration in said residual gas mixture and keep the combustible gas concentration beyond the range of explosion.

* * * * *